United States Patent [19]

Watanabe et al.

[11] 3,973,725
[45] Aug. 10, 1976

[54] APPARATUS FOR DISCRIMINATING THE TYPE OF WHITE BLOOD CORPUSLES AND FOR COUNTING THE NUMBER THEREOF

[75] Inventors: Sadakazu Watanabe, Kawasaki; Hidenori Shinoda, Yokohama; Yuichi Imasato, Tokyo, all of Japan

[73] Assignee: Tokyo Shibaura Electric Co., Ltd., Kawasaki, Japan

[22] Filed: Nov. 12, 1974

[21] Appl. No.: 523,077

[30] Foreign Application Priority Data
Nov. 13, 1973  Japan.............................. 48-126781

[52] U.S. Cl.......................... 235/92 PC; 235/92 R; 235/151.3; 356/39
[51] Int. Cl.$^2$....................................... G06M 11/00
[58] Field of Search..................... 235/92 PC, 151.3; 356/39

[56] References Cited
UNITED STATES PATENTS

| | | | |
|---|---|---|---|
| 3,315,229 | 4/1969 | Smithline............................. | 356/39 |
| 3,714,372 | 1/1973 | Rosen et al........................... | 356/39 |
| 3,748,044 | 7/1973 | Liston................................. | 356/39 |
| 3,824,393 | 7/1974 | Brain.................................. | 356/39 |

Primary Examiner—Joseph M. Thesz
Attorney, Agent, or Firm—Cushman, Darby & Cushman

[57] ABSTRACT

The apparatus comprises an illuminating system including a rotary filter for spectrum-analyzing a sample containing white blood corpuscles subjected to WRIGHT staining process, for example, and mounted on a glass slide, into monochromatic lights having different wavelengths in the visible light range, a video camera for scanning a predetermined area of the spectrum-analyzed sample for producing a picture image, a photoelectric transducer for producing an electric signal corresponding to the tone of the picture image at the sampling point in the predetermined area, a digital-analogue converter for converting the electric signal into a digital signal, a memory device for storing the output from the digital-analogue converter, a circuit for normalizing the information stored in the memory device, similarity calculating circuit for determining the similarity between the output from the normalyzing circuit and reference data, means for detecting and storing the types of the white blood corpuscles respectively corresponding to the maximum value and the value next to the maximum of the similarity thus determined, means for classifying the sampling points of each type of the white blood corpuscles and counting the number of the sampling points, and means for estimating the number of the white blood corpuscles of each type in the predetermined area based on the nunber of the sampling points.

13 Claims, 20 Drawing Figures

F I G. 13
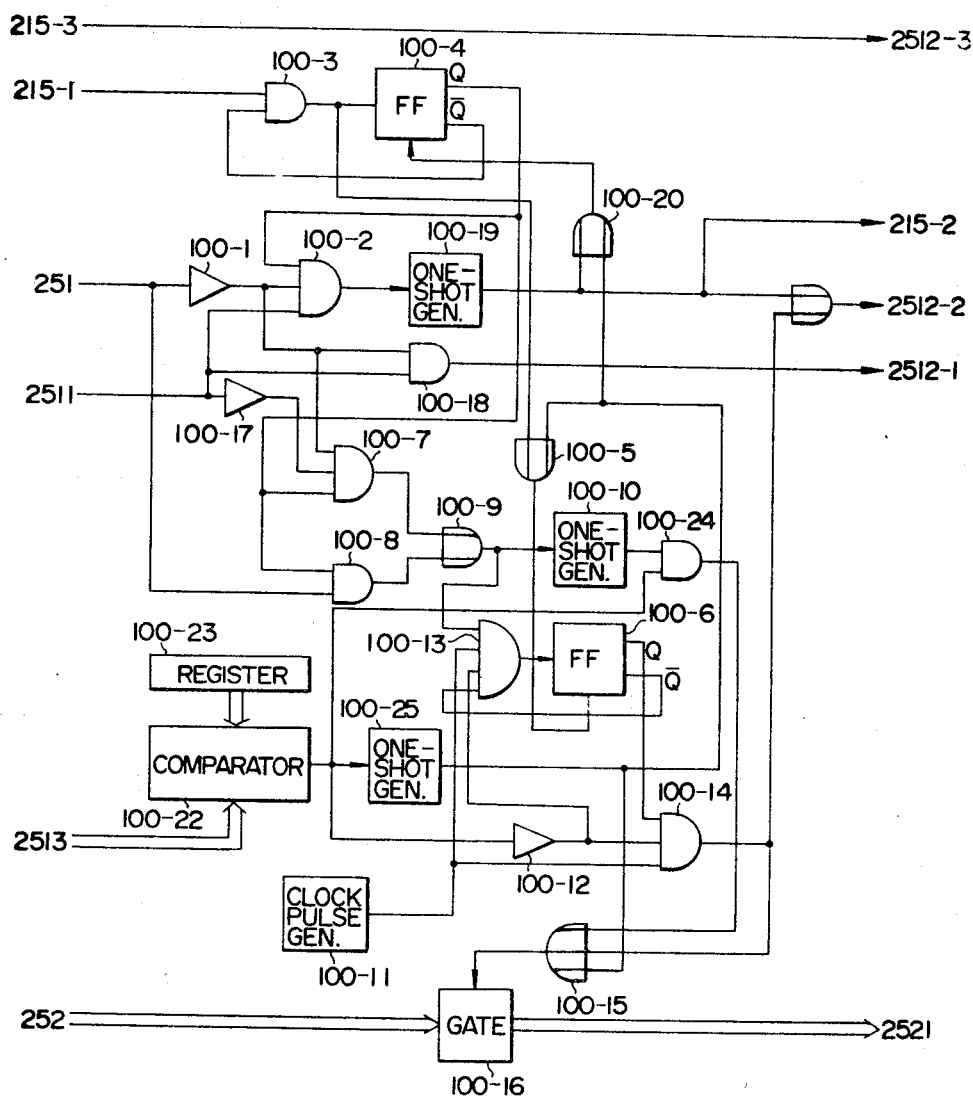

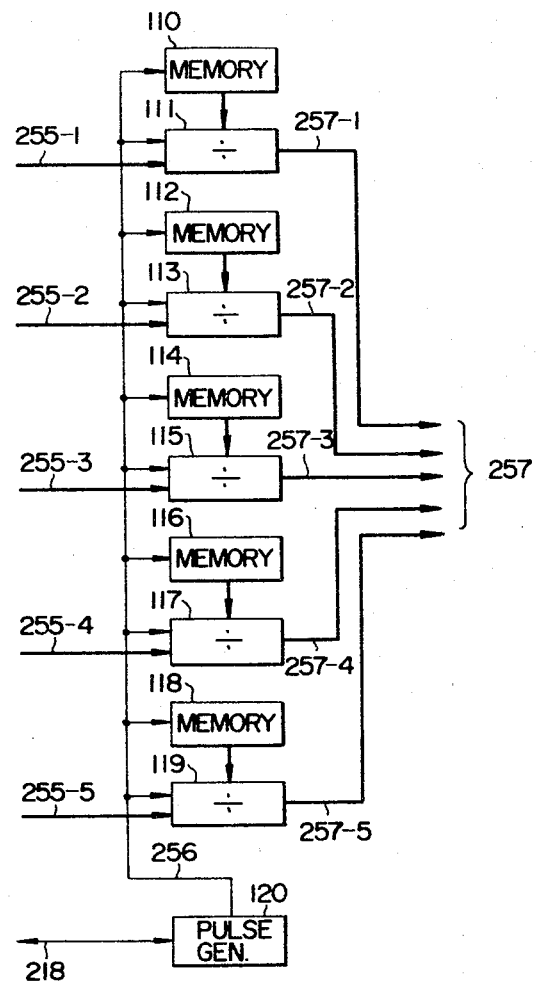

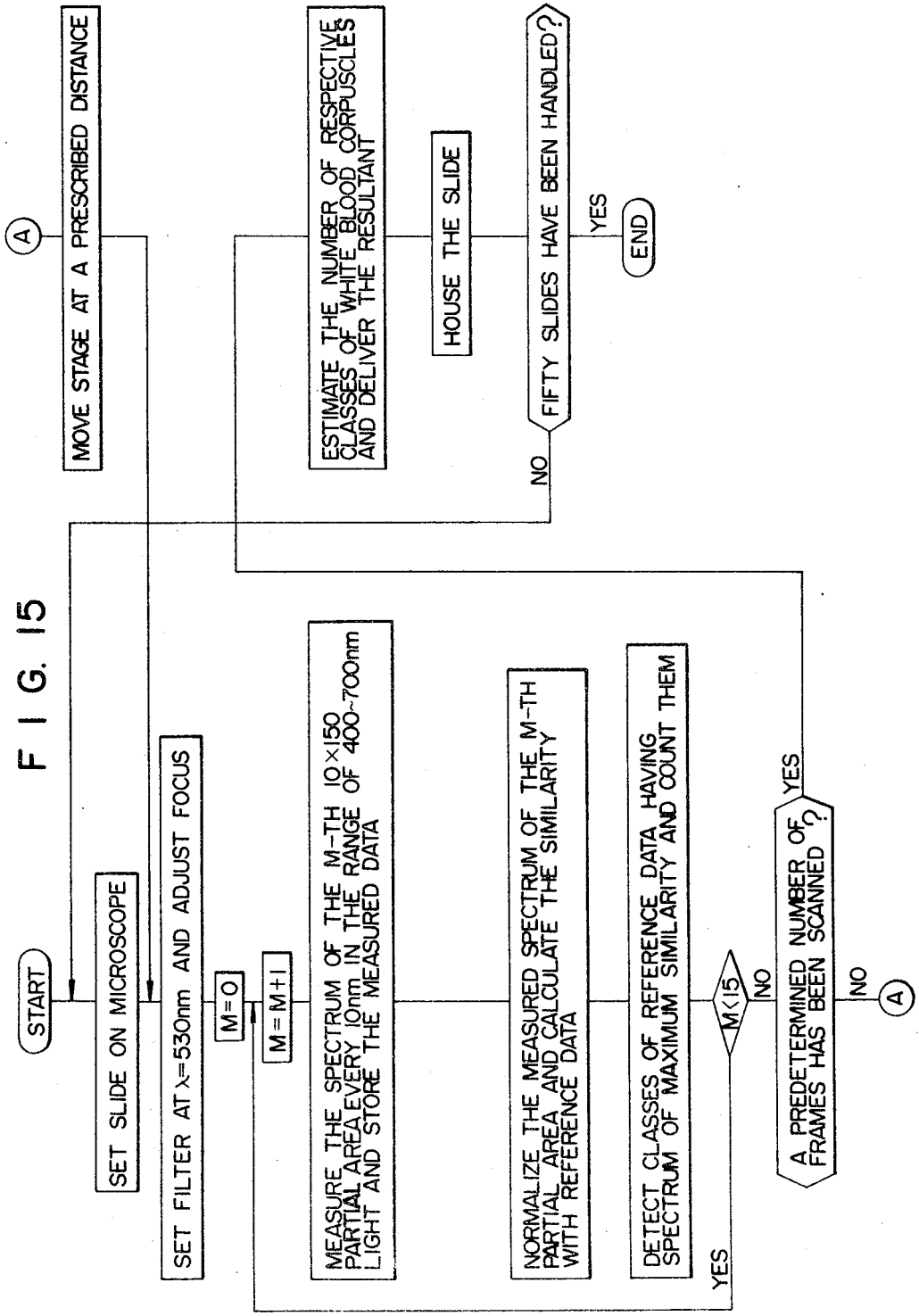

APPARATUS FOR DISCRIMINATING THE TYPE OF WHITE BLOOD CORPUSLES AND FOR COUNTING THE NUMBER THEREOF

BACKGROUND OF THE INVENTION

This invention relates to apparatus for discriminating and counting white blood corpuscles and more particularly to apparatus for discriminating the types of white blood corpuscles and counting the number thereof according to the type by utilizing different absorption spectrum of different types of white blood corpuscles.

The methods of examining blood which are important for clinic chemical examinations are classified into a number of types. Most common clinical examination includes such items as the hematocrit measurement, hemoglobin measurement, counting of the number of red blood corpuscles, counting of the number of reticulocytes and discrimination and counting of the number of white blood corpuscles. Of these various items, items other than the counting of the number of reticulocytes and the discrimination and counting of the white blood corpuscles, the classification thereof being based on the pattern of blood cells, have already been automatized and are now being used in many large hospitals. However, as it is necessary to discriminate respective patterns of the blood corpuscles of both types for the purpose of counting the number of the reticulocytes and discriminating and counting the number of white blood corpuscles it is difficult to automatize these operations.

According to the conventional method of discriminating and counting the white blood corpuscles the operator discriminates and counts the number of white blood corpuscles of different types while observing a microscope. Usually, 100 to 200 white blood corpuscles per one slide are examined to determine the percentage of respective types of the white blood corpuscles, and it takes about five minutes to examine one slide. The operation of classifying and counting the number of the white blood corpuscles while adjusting the stage for the slide and the focus of the microscope requires a large labor and accompanying tiredness. For this reason, the number of the slides that can be examined by the operator in one day is only 20.

Normal white blood corpuscle cells contained in terminal venous blood which is used for standard examination are classified into neutrophils, eosinophils, basophils, lymphocytes and monocytes and then the numbers thereof are counted independently. The percentage of the number of white blood corpuscles of each type to the total number of the white blood corpuscles is relatively constant in a definite range for healthy adults, but the frequency of the appearance thereof is greatly influenced by stress, injury, diseases, poisons, radiation damage, etc. Such variation of the frequency is called as non-unique reaction and is not only effective to judge the presence or absence of a disease but also important to judge the type and degree of the diseases and to determine the method of aftercare and remedy. This increases the load of the operator so that partial or full automation of such examination is highly desirable. Such automation is also desirable to treat a number of patients in a short time not only in group diagnosis and overall health control systems but also in the screening of patients.

The following prior methods have been proposed to meet this requirement for automation. According to one method called flow system, the fact that white blood corpuscles can be stained with different colours according to their type is utilized and different methods of staining are used for different types of the white blood corpuscles for the purpose of discrimination and counting. According to another method pattern discriminating technique is utilized. Thus video signals of blood corpuscle images are formed by photographing a blood smear coated on a glass slide through a microscope and a vidicon camera, and then the video signals are analyzed for the purpose of discrimination and counting. However, according to the flow system since the discrimination and counting are performed by passing stained blood through a test tube, it is necessary to use a large quantity of blood. Moreover, when it is desired to inspect again the sample in later days it is necessary to again sample and stain blood. According to the latter method since the white blood corpuscles are classified according to the size of nuclei, pattern, density, concentration size and colour of the cellar substances it is necessary to use a plurality of large capacity memory devices for storing these information items.

SUMMARY OF THE INVENTION

Accordingly, it is an object of this invention to provide a novel apparatus of discriminating the type and counting the number of white blood corpuscles which can eliminate various difficulties of the prior art apparatus, can use the standard form of sample on a glass slide and can be constructed compact and inexpensive.

According to this invention there is provided apparatus for discriminating the type and counting the number of white blood corpuscles comprising means for irradiating with light a predetermined area of a slide supporting stained white blood corpuscles, means for obtaining an information regarding the image of the white blood corpuscles which is analyzed into respective wavelength components over the entire range of visible lights, means for obtaining the similarity between the image information and sample data and means responsive to the resulting similarity for discriminating the types of the white blood corpuscles and counting the number of the white blood corpuscles of each type.

According to a preferred embodiment of this invention, a glass slide deposited with a blood smear which is stained by conventional staining process is irradiated with light and the spectrum of the image of the white blood corpuscles formed by a microscope is analyzed by means of a rotary type continuous interference filter over the entire range of visible light. The analyzed image of the white blood corpuscles is picked up by a vidicon tube to form a video signal corresponding to the white blood corpuscle image. This video signal is then converted into a digital signal by a digital-analogue converter. If necessary, the digital signal is then normalized and the similarity between the normalized digital signal and a reference spectrum data is determined. A circuit is provided for judging whether the difference between the maximum value and the value next to the maximum of the similarity is larger than a predetermined threshold value or not and in the former case for judging that the type of the white blood corpuscles is the type that represents the reference spectrum data. The number of the white blood corpuscles judged in this manner is counted by a counter and the result of the counting is used to estimate the total number of the white blood corpuscles of respective types by using the theory of statistics.

BRIEF DESCRIPTION OF THE DRAWING

This invention can be more fully understood from the following detailed description when taken in conjunction with the accompanying drawings, in which:

FIG. 13 is a block circuit diagram showing one example of the operation control circuit shown in FIG. 12;

FIG. 14 is a block circuit diagram showing one example of the estimation circuit shown in FIG. 1; and FIG. 15 is a flow chart showing the order of operations which are performed for discriminating and counting the number of white blood corpuscles by using the novel apparatus of this invention.

DESCRIPTION OF THE PREFERRED EMBODIMENTS

Figure 1:
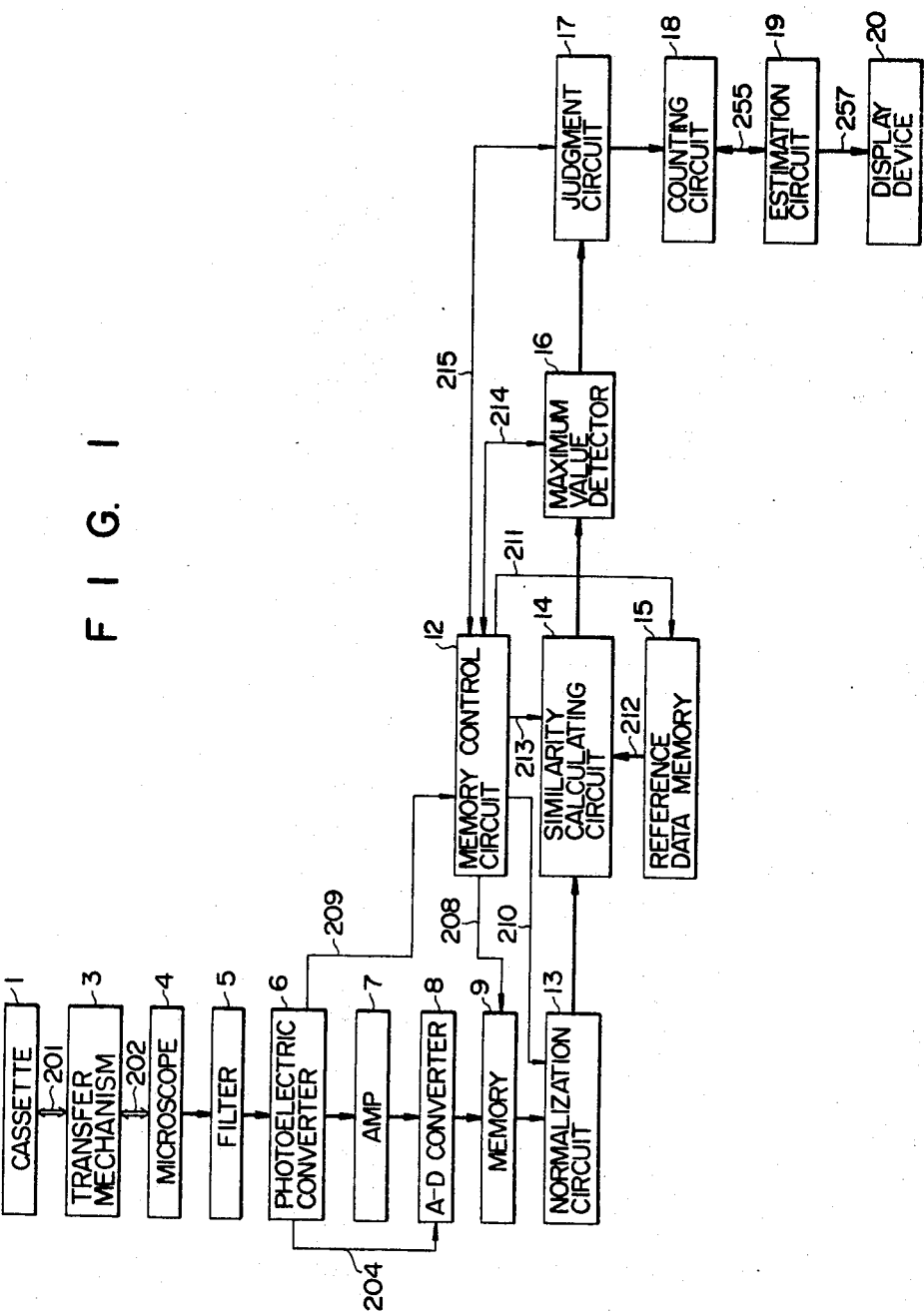
FIG. 1 is a block diagram showing the basic construction of one embodiment of this invention.
Figure 2:
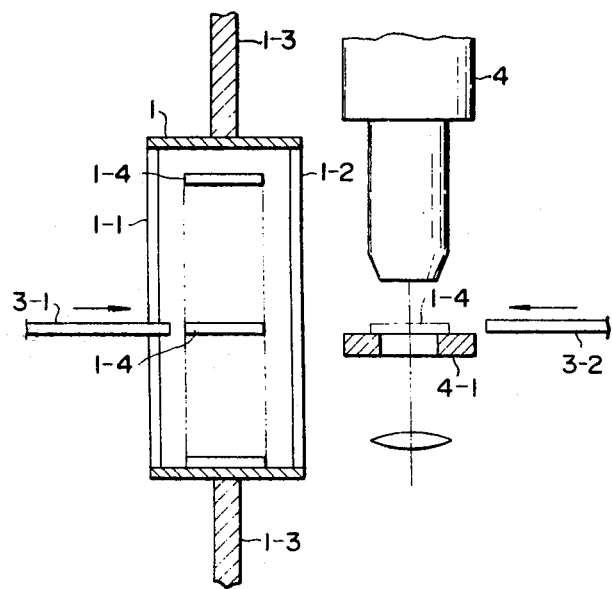
FIG. 2 schematically shows the cassette and the mechanism for exchanging a slide utilized in the block diagram shown in FIG. 1.

The preferred embodiment of this invention diagrammatically illustrated in FIG. 1 comprises a cassette 1 containing a plurality of glass slides (not shown) coated with blood smears stained by WRIGHT-STAIN method. The number of the slides contained in the cassette 1 is 50, for example. The slides in the cassette 1 are set, one after one, on the stage of a microscope 4 by means of a transfer mechanism and the slide which has undergone the examination is returned to the cassette 1 by the transfer mechanism 3. As shown in FIG. 2, the cassette 1 comprises a box having opposed side walls provided with slits 1-1 and 1-2. Feed screws 1-3 are connected to the upper and bottom walls of the box. Fifty slides 1-4 are contained in the cassette 1. As the feed screws 1-3 are rotated the cassette 1 is moved in the vertical direction. When the cassette 1 is stopped at a predetermined position, a push rod 3-1 of the transfer mechanism 3 is moved to the right to transfer a desired one of the slides 1-4 onto the stage 4-1 of the microscope 4. When the slide 1-4 set on the stage 4-1 of the microscope is treated in a prescribed manner (to be described later), a second push rod 3-2 of the transfer mechanism 3 is moved to the left to return the slide 1-4 back to the cassette 1. Lines 201 and 202 shown in FIG. 1 show the movement of the slide 1-4 described above.

Figure 4:
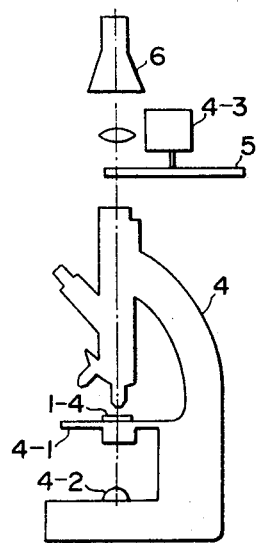
FIG. 4 is a diagrammatic representation of the optical system including a microscope and utilized in the block diagram shown in FIG. 1.

Turning back again to FIG. 1, the slide set on the stage of the microscope 4 is illuminated by the light from a source of light (not shown) positioned at a predetermined position, to send a microscopic image of the white blood corpuscles to a rotary type optical interference filter 5. The optical system has a construction as diagrammatically shown in FIG. 4. Thus, the source of light 4-2 is positioned beneath the stage 4-1 of the microscope 4 for illuminating from under the slide 1-4 mounted on the stage 4-1. The microscopic image of the white blood corpuscles on the slide 1-4 passes through a monochromatic filter of a predetermined wavelength of the rotary type linear interference optical filter 5 rotated by a pulse motor 4-3 to undergo spectral analysis. The analyzed spectra are focussed on a suitable photoelectric transducer, for example the face plate of an image orthicon. The filter 5 is a rotary type continuous interference filter for performing spectral analysis of the lights having a continuous wavelength of from 400 nm to 700 nm. The pulse motor 4-3 is stepped a predetermined angle for each frame of the image orthicon in synchronism with a vertical synchronizing signal, for example, thereby rotating the filter 5 to set the filter for the next wave-length of the monochromatic light. The reason that an image orthicon is used as the photoelectric transducer lies in that the number of frames per unit time is large and that the ghost image is very small. As the source of light 4-2 is used a lamp which produces a spectrum that can compensate for the variation in the sensitivity of the image orthicon caused by the variation in the wavelength of the light thereby assuming a flat output over the entire range of the visible light.

Figure 3A:
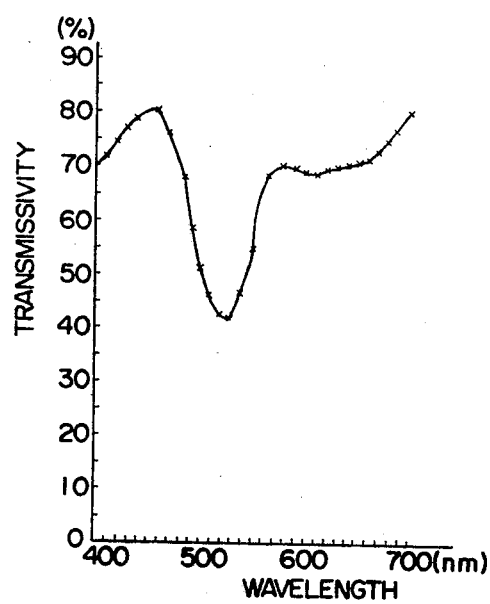
FIGS. 3A through 3F are graphs showing the absorption spectra of various types of white blood corpuscles for visible lights.
Figure 3B:
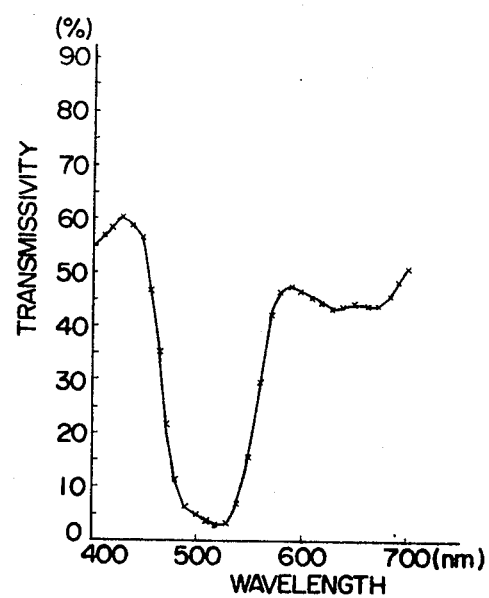
Figure 3C:
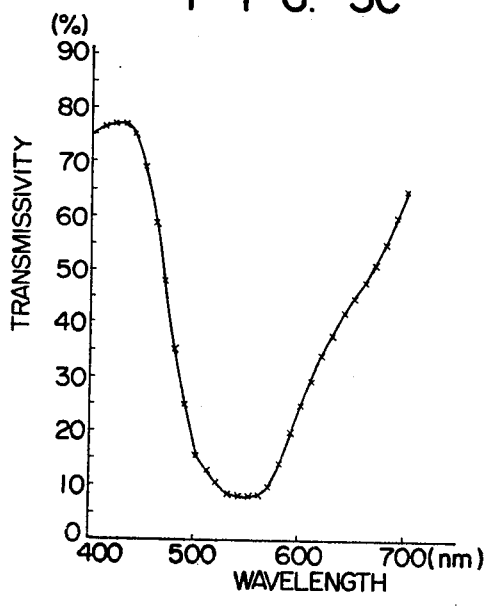
Figure 3D:
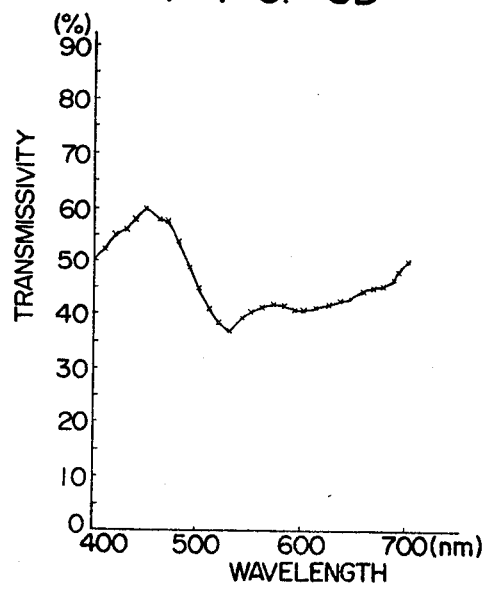
Figure 3E:
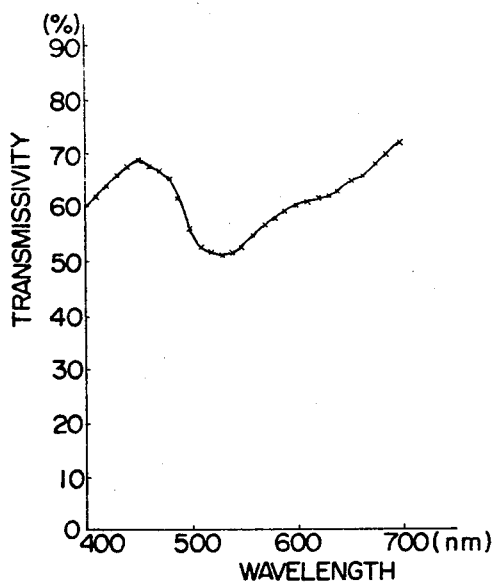
Figure 3F:
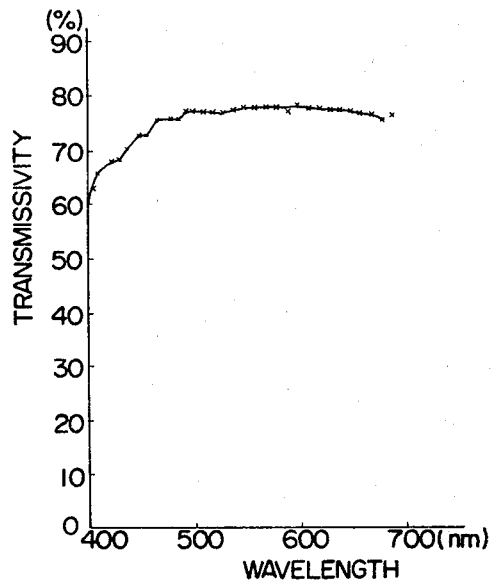

FIGS. 3A through 3F illustrate spectral characteristic curves obtained by the cellar substance of the white blood corpuscles, in which the abscissa represents the wavelength of the light used to irradiate the sample and the ordinate the transmissivity of the light projected upon the white blood corpuscles. FIG. 3A shows the spectral characteristic of neutrophils, FIG. 3B that of eosinophils, FIG. 3C that of basophils, FIG. 3D that of lymphocytes, and FIG. 3E that of monocytes. FIG. 3F shows the spectral characteristic of a glass slide coated with a sample of white blood corpuscles. As can be noted from FIGS. 3A through 3E, white blood corpuscles of all types show a remarkable absorption peak for monochromatic light having a wavelength of about 530 nm, but absolute transmissivity varies greatly depending upon the type of the white blood corpuscles. Further each characteristic curve has peculiar configuration. For this reason, it is possible to classify the white blood corpuscles according to the configuration of the characteristic curve.

Referring again to FIG. 1, the video signal having a level corresponding to the tone or density of the white blood corpuscle image produced by the photoelectric converter 6 including the image orthicon is amplified by a video amplifier 7 and then converted into a digital signal by an analogue-digital (A-D) converter 8. In this example, it is assumed that the digital signal consists of 8 bits. The timing for sampling the A-D converter 8 is formed by a synchronizing signal supplied from the image orthicon via a conductor 204.

The 8-bit digital signal formed by the A-D converter 8 is sent to a memory device 9 and stored therein each time the wavelength of the monochromatic light is varied at each sampling point. The address of the memory device 9 corresponding to the sampling point is designated by the memory control device 12 through a conductor 208. As will be described later, the memory control device 12 receives a synchronizing signal from the photoelectric converter 6.

In this example, the image of the sample on the glass slide comprises 150 × 150 sampling points in one frame of the image orthicon. For the purpose of decreasing the capacity of the memory 9 these sampling points are divided into 15 subareas each consisting of 10 × 150 points. Fifteen subareas are successively processed to obtain full data of one picture frame.

When the data of the sampling points corresponding to 1 subarea are obtained the spectral data regarding 10 × 150 points are successively sent to a normalization circuit 13 to be normalized thereby by the action of a timing signal sent from the memory control circuit 12.

Figure 5:
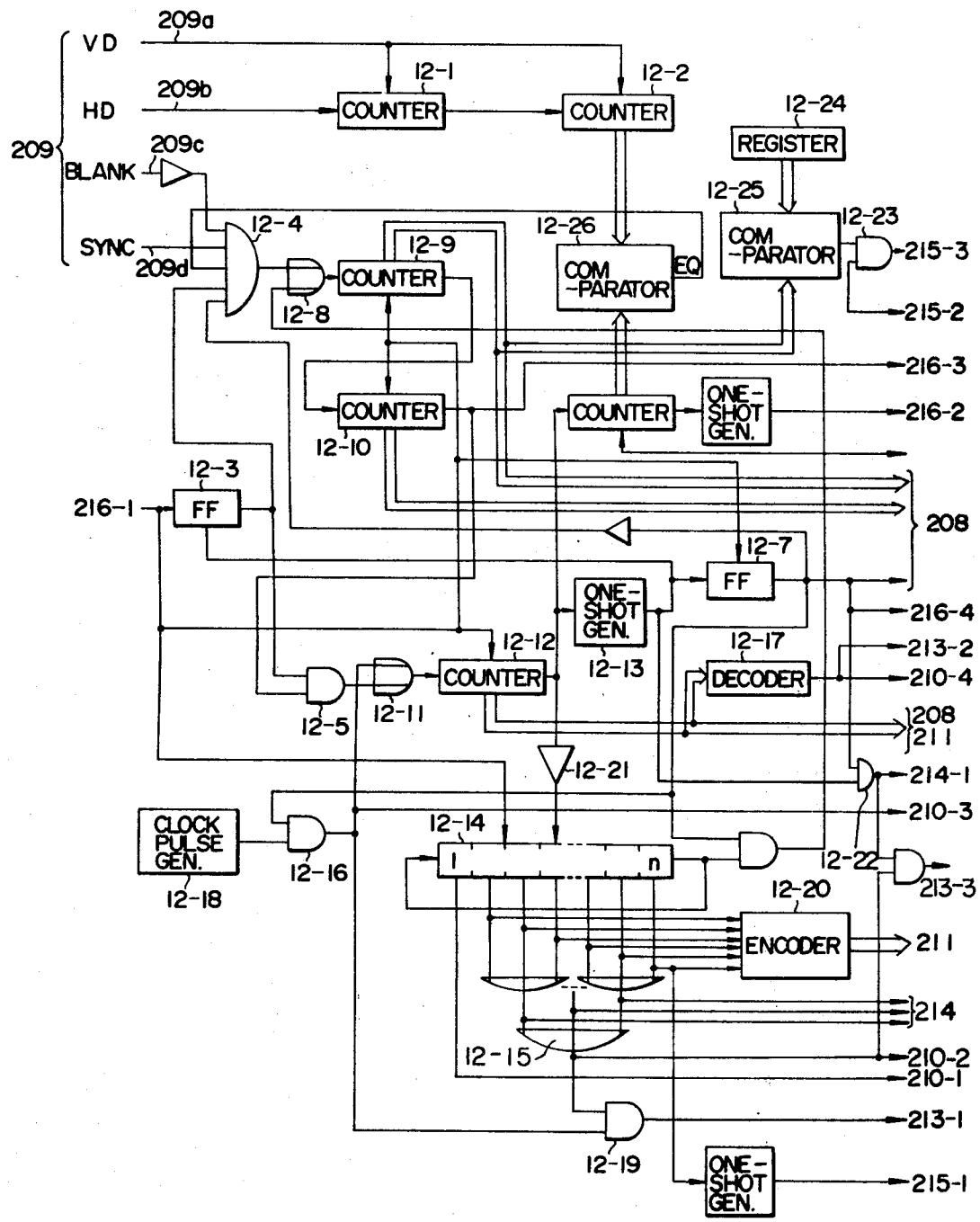
FIG. 5 is a block circuit diagram showing one example of the memory control circuit shown in FIG. 1.

One example of the memory control circuit 12 is illustrated in FIG. 5. The vertical synchronizing signal sent from the image orthicon of the photoelectric converter 6 over a conductor 209a is applied to the clear terminals of a decimal counter 12-1 and a 15-step counter 12-2.

frame is written in the memory device 9, the 31-step counter 12-12 is stepped one step by a carry signal from the counter 12-10 whereby the data regarding the next wavelength of monochromatic light are stored in the memory device 9. When the data-memorizing operation regarding a total of 31 monochromatic lights has completed, the 31-step counter 12-12 sends a carry signal to a one-shot generator 12-13 which produces one output in response to the build-down of the carry signal thereby setting flip-flop circuit 12-3 and setting flip-flop circuit 12-7.

Presence of a set output from the flip-flop circuit 12-7 represents the read mode of the memory device 9 whereas absence of the set output represents the write mode. This output is also sent to the memory device 9 over the conductor 208.

As has been described hereinabove, the spectral data comprise 31 sets over a range of the wavelength of from 400 nm to 700 nm in the visible range and spaced 10 nm from each other. Let us represent each set by $f(\lambda i)$, where $i = 0, 1, 2 \ldots 30$, and $\lambda_0 = 400$ nm, $\lambda_1 = 410$ nm, ... $\lambda_{30} = 700$ nm, then the normalization of the data is performed in the following manner. Thus, the normalization is effected by determining a function $F(\lambda i)$ which is expressed by $$F(\lambda i) = \frac{f(\lambda i) - f_{min}}{\sqrt{\frac{10}{3} \sum_{j=0}^{29} \{f^2(\lambda j) + f(\lambda j)f(\lambda_{j+1}) + f^2(\lambda_{j+1}) + 3f_{min}[f_{min} - f(\lambda j) + f(\lambda_{j+1})]\}}} \quad (1)$$

The decimal or 10-step counter 12-1 produces a carry signal each time it counts 10 horizontal synchronizing signals sent over conductor 209b and the carry signal is counted by the 15-step counter 12.2. When the spectral data regarding 10 × 150 points are produced the decimal counter 12-1 produces a carry signal thus increasing by one count the content of the 15-step cunter 15-2. The count of the counter 12-2 represents the number of the subareas in one frame which is divided into 15 equal areas. When a write signal for the memory device 9 appears on a conductor 216-1, a flip-flop circuit 12-3 is set and its set output is applied to inputs of AND gate circuits 12-4 and 12-5, respectively. To the remaining inputs of the AND gate circuit 12-4 are applied the inverted signal of a blanking signal from the photoelectric converter 6, the output from a comparator 12-6, a synchronizing signal having the same frequency as the number of samplings during one field period, and the inverted signal of the output from the flip-flop circuit 12-7. The output from the AND gate circuit 12-4 is coupled to a 150-step counter 12-9 via an OR gate circuit 12-8 for sequentially counting 150 addresses in the direction of lines of the memory device 9. The decimal counter 12-10 is used to count the number of the addresses in the direction of columns of the memory device 9 and is advanced one step in accordance with the carry signal from the 150-step counter 12-9. Two output lines indicated by thick lines from counters 12-9 and 12-10 are connected to the memory device 9 via a conductor 208 to send address information.

Figure 6:
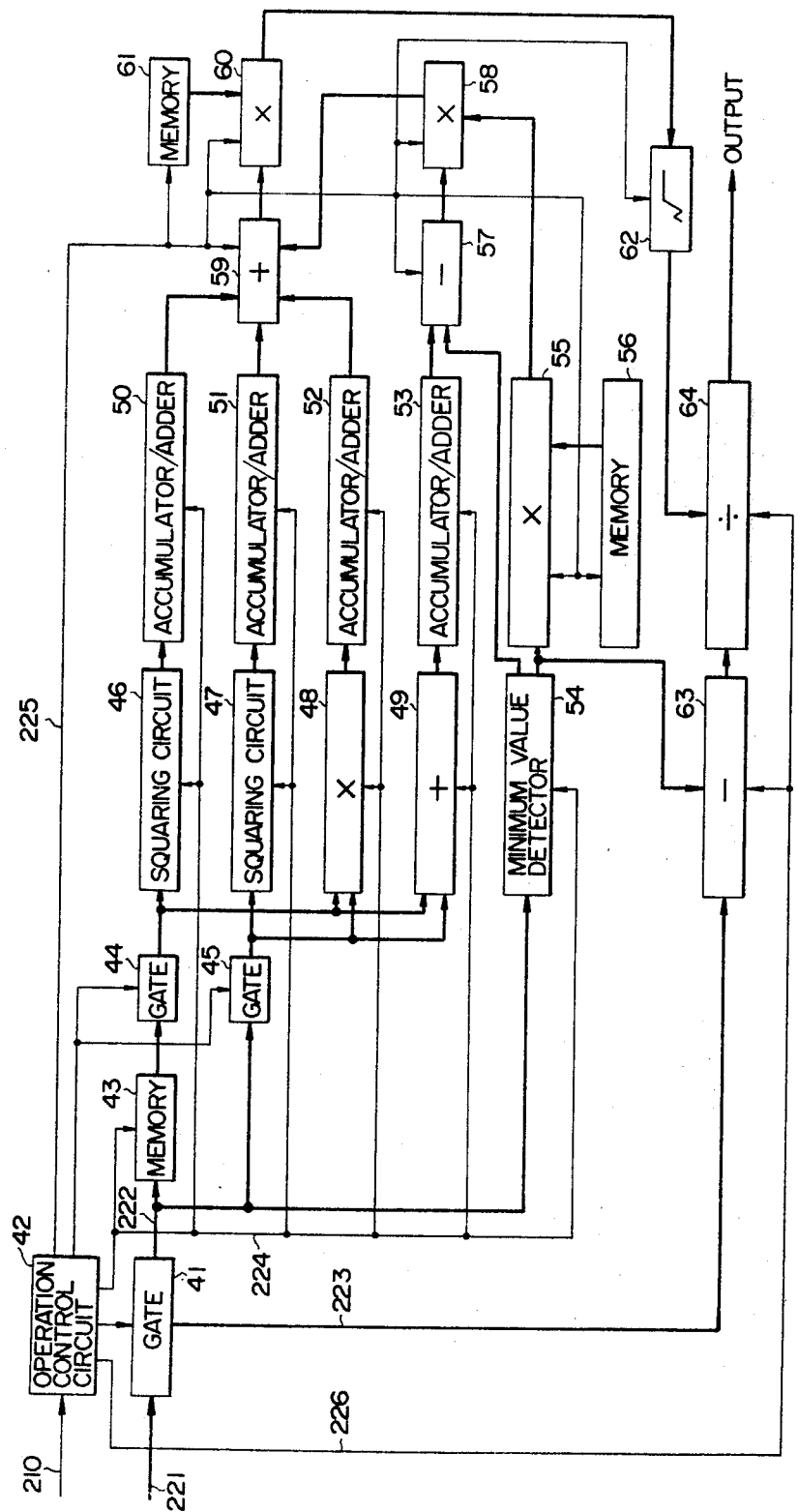
FIG. 6 is a block circuit diagram showing one example of the normalization circuit shown in FIG. 1.
Figure 7:
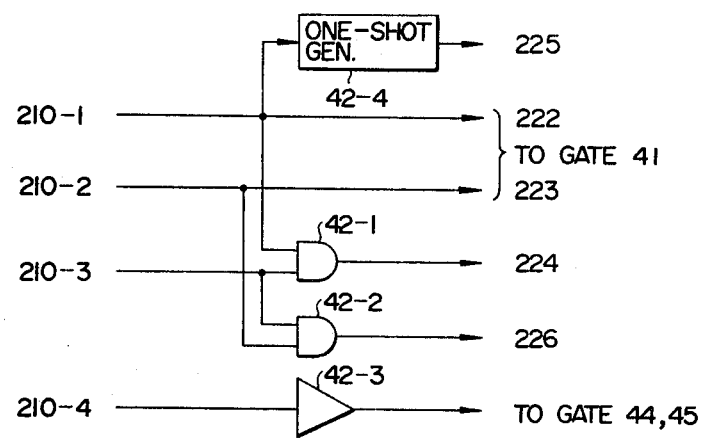
FIG. 7 is a block circuit diagram showing one example of the operation control circuit shown in FIG. 6.

The other input of the AND gate circuit 12-5 is connected to receive the carry signal from the decimal counter 12-10 so that each time when the information regarding 10 × 150 sampling points is stored in the memory device 9, a step signal is sent to a 31-step counter 12-12 from the AND gate circuit 12-5 through an OR gate circuit 12-11. When the information of one where $f_{min}$ represents the minimum value of $f(\lambda i)$ and $i = 0, 1, 2 \ldots 30$.

for $F(\lambda i)$ $$\frac{10}{3} \sum_{i=0}^{29} F^2(\lambda i) + F(\lambda i)F(\lambda_{i+1}) + F^2(\lambda_{i+1}) = 1 \quad (2)$$

with reference now to FIG. 6, the detail of the nomalization circuit 13 constructed to calculate equation (1) will be described. The data stored in the memory device 9 shown in FIG. 1 are applied to a gate circuit 41 shown in FIG. 6 over conductor 210. Under the control of an operation control circuit 42 the gate circuit 41 determines that whether it should apply its output to a conductor 222 or conductor 223. Actually however, the construction is such that the signals sent from the memory control circuit 12 shown in FIG. 5 over two conductors 210-1 and 210-2 are applied to the control terminals of the gate circuit 41 through conductors 222 and 223 as shown in FIG. 7. More particularly, in FIG. 5, the signal of the left-hand end bit of a n-step ring counter 12-14 is applied to the conductor 210-1 and the outputs of other bits are applied to the conductor 210-2 through an OR gate circuit 12-15. The signal appearing on the conductor 210-1 is an initiation signal preciding a reference pattern, whereas the signal appearing on the conductor 210-2 indicates that either one of the reference patterns is being processed.

Turning back to FIG. 6, the data on the conductor 222 are conducted to a memory device 43 having a capacity that can store one set of data for sending to a gate circuit 44 one step preceding the set of data on the conductor 222 in accordance with the timing pulse from the operation control circuit 42. More particularly, where a signal appears on a conductor 210-3 shown in FIG. 7, a signal is sent to the memory device 43 from AND gate circuit 42-1 over the conductor 224 thus sending the content of the memory device 43 to the gate circuit 44. Then, the succeeding data are stored in the memory 43. Where a signal appears at this time on the conductor 210-4 shown in FIG. 7, the output from an inverter 42-3 changes to 0 state thus disenabling gate circuits 44 and 45. At this time, the output from the AND gate circuit 12-16 shown in FIG. 5 is applied to the conductor 210-3 whereas the output from a decoder 12-17 is applied to a conductor 210-4. The AND gate circuit 12-16 is enabled when the flip-flop circuit 12-7 is set to the read mode to send the clock pulse generated by clock pulse generator 12-18 to the conductor 210-3 and to one input of an AND gate circuit 12-19. At the same time, the content of the 31-step counter 12-12 is detected by the decoder 12-17 and the output thereof is applied to the inverter 42-3 shown in FIG. 7 over the conductor 210-4.

The gate circuits 44 and 45 of FIG. 6 are controlled by the operation control circuit 42 such that they are disenabled or closed when the first set of data is applied to the operation control circuit 42 so as to prevent passage of the signal. As a consequence, after the data regarding the second monochromatic filter, when the $i$-th set of data is applied the gate circuit 44 produces the $(i-1)$-th data whereas gate circuit 45 the $i$-th data. The output signals from the gate circuits 44 and 45 are applied to squaring circuits 46 and 47, respectively, and to multiplying circuit 48 and addition circuit 49 to perform necessary calculations. The outputs from the squaring circuits 46 and 47, multiplying circuit 48 and addition circuit 49 are respectively applied to adders 50, 51, 52 and 53 each including an accumulator. Each one of these accumulator-adders 50, 51, 52 and 53 functions to add the content of the accumulator to the input data and then stores again the sum in the accumulator. The timings of the operations of the squaring circuits 46 and 47, multiplying circuit 48, addition circuit 49 and accumulator-adders 50, 51, 52 and 53 are controlled by the clock pulse supplied through the AND gate circuit 42-1 of the operation control circuit 42. The output of the gate circuit 41 is sent to a minimum value detector 54 for detecting the minimum value in the data.

Figure 8:
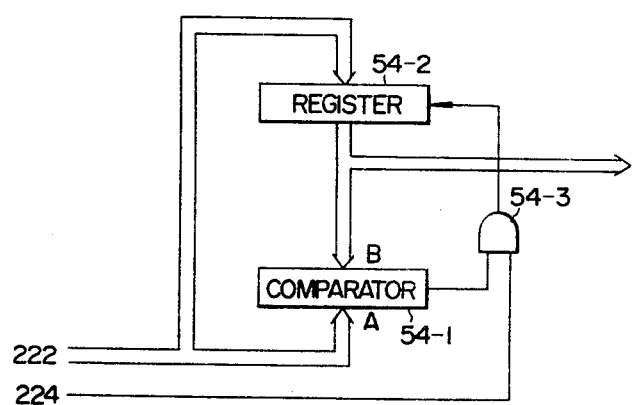
FIG. 8 is a block circuit diagram showing one example of the minimum value detector shown in FIG. 6.

As shown in FIG. 8, the minimum value detector 54 comprises a comparator 54-1, a register 54-2 and an AND gate circuit 54-3. Thus, the comparator 54-1 operates to compare the data stored in the register 54-2 with the data newly sent over the conductor 222 so as to send a gating signal to the AND gate circuit 54-3 only when the new data is smaller than the data stored in the register 54-2. The clock signal from a conductor 224 is applied to the register 54-2 to act as the load signal. In response to this load signal the register 54-2 operates to store a new smaller signal. In this manner, the smaller signals are successively stored in the register 54-2 with the result that data of the minimum value are stored in the register 54-2.

The minimum data stored in the minimum value detector 54 in this manner are sent to the multiplying circuit 55 shown in FIG. 6 to obtain a product of the minimum data and a constant corresponding to one set of data and stored in the memory device 56. The minimum data are also sent to a subtractor 57 to obtain the difference between the minimum data and the output from the accumulator-adder 53. The timings of the operations of the minimum value detector 54, multiplying circuit 55 and memory device 56 are made to coincide with the timing of the clock pulse sent over the conductor 224. The difference signal produced by the subtractor 57 is sent to a multiplying circuit 58 to be multiplied by the output from the multiplying circuit 55. When all of the accumulator-adders 50, 51 and 52, and multiplying circuit 58 complete their operations, the outputs thereof are sent to addition circuit 59 to obtain the sum of the outputs. This result is sent to a multiplying circuit 60 where it is multiplied by a constant corresponding to one set of data and has been stored in a memory device 61. The output from the multiplying circuit 60 is sent to a square root circuit 62. The timings of the operations of the subtraction circuit 57, multiplying circuit 58, addition circuit 59, multiplying circuit 60 and square root circuit 62 are provided by the output of the one-shot generator 42-4 in the operation control circuit shown in FIG. 7, which is applied to these operating circuits through a conductor 225. In this manner, the value of the denominator of equation (1) can be calculated.

The signal from the OR gate circuit 12-15 of the memory control circuit 12 shown in FIG. 5 is sent to the gate circuit 41 through a conductor 210-2 shown in FIG. 7 so that the gate circuit 41 produces data on a conductor 223. Again 31 spectral data are read out from the memory device 9 shown in FIG. 1 and applied to the subtraction circuit 63 in which the difference between the input data and the minimum value data produced by the minimum value detector 54 is obtained. The difference value is sent to a division circuit 64 in which the output from the subtraction circuit 63 is divided by the value of the denominator of the equation (1) which has been calculated as described above. The timings of the operations of the subtraction circuit 63 and division circuit 64 are determined by the output of the AND gate circuit 42-2 in the operation control circuit 42 shown in FIG. 7 and applied to the operation circuits through a conductor 226.

The data normalized as described hereinabove are applied to a similarity calculating circuit 14 shown in FIG. 1 from the division circuit 64 shown in FIG. 6. In the similarity calculating circuit 14, the similarity S between the normalized data and the reference spectral data which have been stored in a reference data memory 15 (several such reference spectral data are used for each type of the white blood corpuscles) is determined by a well known equation $$S = \frac{10}{3} \sum_{i=0}^{29} \{ [F(\lambda_i)+F(\lambda_{i+1})][G(\lambda_i)+G(\lambda_{i+1})]$$

$$+F(\lambda_i)G(\lambda_i)+F(\lambda_{i+1})G(\lambda_{i+1}) \} \quad (3)$$

The similarity S has a value expressed by $0 \leq S \leq 1$. Equation (3) for determining the similarity S utilizes a well known procedure to obtain an inner product. The reference data memory device 15 is controlled by the memory control circuit 12 through a conductor 211 for sending reference spectral data to the similarity calculating circuit 14 through a conductor 212 each time spectral data are applied to the similarity calculating circuit 14 from the normalization circuit 13. The timing of the operation of the similarity calculating circuit 14 is controlled by the clock pulse applied by the memory control circuit 12 through a conductor 213.

Figure 9:
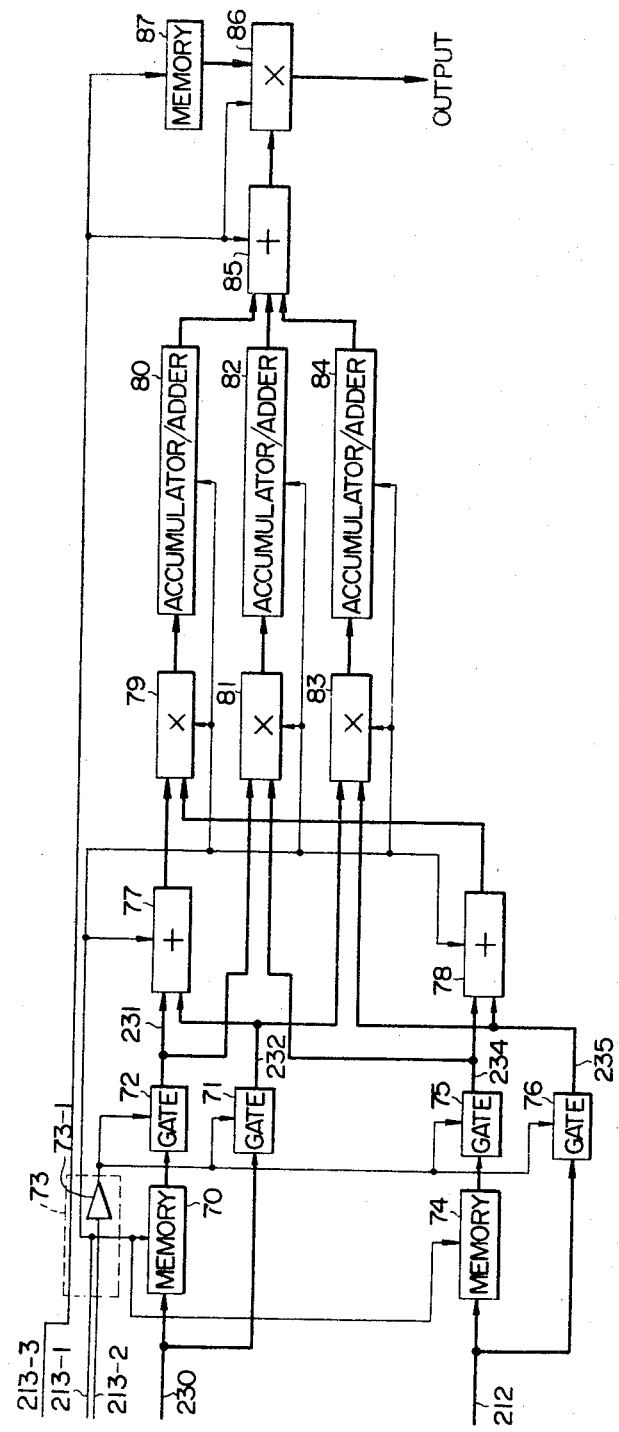
FIG. 9 is a block diagram showing one example of the similarity calculating circuit shown in FIG. 1.

The output from the normalization circuit 13 is sent to the one-set data memory device 70 of the similarity calculating circuit 14 shown in FIG. 9 from the division circuit 64 shown in FIG. 6 through a conductor 230 and to a gate circuit 71. The memory device 70 is provided for the purpose of producing data which are delayed one step just like the memory device 43 of the normalization circuit 13. The output of the memory device 70 is sent to a gate circuit 72. The gate circuits 71 and 72 are connected to receive the output of the decoder 12-17 of the memory control circuit shown in FIG. 5 through an inverter 73-1 of the operation control circuit 73 and a conductor 213-2. The decoder 12-17 is constructed to produce an output when the content of the 31-step counter 12-12 becomes to 0 and when this output is inverted by an inverter 73-1, the gate circuits 71 and 72 are disenabled or closed. More particularly, the gate circuits 71 and 72 operate not to produce any output on conductors 231 and 232 when data corresponding to the first monochromatic light having a frequency of 400 nm is applied thereto. The operation control circuit 73 applies a clock pulse to the memory devices 70, 74 and 80, addition circuits 77, 78 and 85, multiplying circuits 79, 81, 83 and 86 and accumulator-adders 80, 82 and 84 through an AND gate circuit 12-19 and a conductor 213-1 shown in FIG. 5 to act as the timing signal.

Conductor 212 applies to the memory device 74 for one set of data the normalized spectral data which have been stored in the reference data memory 15 shown in FIG. 1 in synchronism with the measured data on a conductor 230. In FIG. 9, there are also shown gate circuits 75 and 76 which are constructed not to produce the first data for the purpose of producing the ($i$ - 1)-th data on a conductor 234 and the $i$-th data on a conductor 235 while they receive the $i$-th data in the same manner as the gate circuits 71 and 72 described above. Both output signals from the gate circuits 71 and 72 are sent to an addition circuit 77 to produce the sum thereof. In the same manner, the output signals from gate circuits 75 and 76 are sent to an addition circuit 78 to produce the sum thereof. The outputs from both addition circuits 77 and 78 are applied to a multiplier 79 to obtain the product thereof and the product is sent to an adder 80 including an accumulator. The outputs from gate circuits 72 and 75 are sent to a multiplier 81 to obtain the product thereof which is sent to an accumulator-adder 82. Further, the outputs from the gate circuits 71 and 76 are applied to a multiplier 83 and the product of these outputs is applied to an accumulator-adder 84. When the data regarding the 30 filters are added by the accumulator-adders 80, 82 and 84, the outputs from these accumulator-adders 80, 82 and 84 are applied to an addition circuit 85 for obtaining the total sum. This sum is sent to a multiplier 86 and multiplied by a constant which has been stored in a memory device 87 for one set of data. The timing operations of these circuits are performed by a pulse signal sent through a conductor 213-3. The output of the multiplier 86 shows the result of the operation of equation (3), thus representing the similarity S.

Referring again to FIG. 1, the value S obtained by calculating the similarity between the normalized input spectral data and the reference spectral data is then sent to a maximum value detector 16 in which the maximum value S, the value next to the maximum value S, the type or class of the sample manifesting the maximum value of S and that of the sample manifesting the value next to the maximum value S are detected. An information regarding the calculation of the similarity for which one of the types of the same is now being performed is applied to the maximum value detector 16 from the memory control circuit 12 through a conductor 214. More particularly, as shown in FIG. 5, the ring counter 12-14 is advanced one step by a shift signal which is obtained by inverting by an inverter 12-21 the build-down portion of a carry signal produced by the 31-step counter 12-12 each time the filter 5 completes one revolution. The outputs from the ring counter 12-15 are applied to the operation control circuit 90 of the maximum value detector 16 shown in FIG. 10 through the output conductors 214 to act as the signals representing the classes of the data stored in the reference memory device 15.

Figure 10:
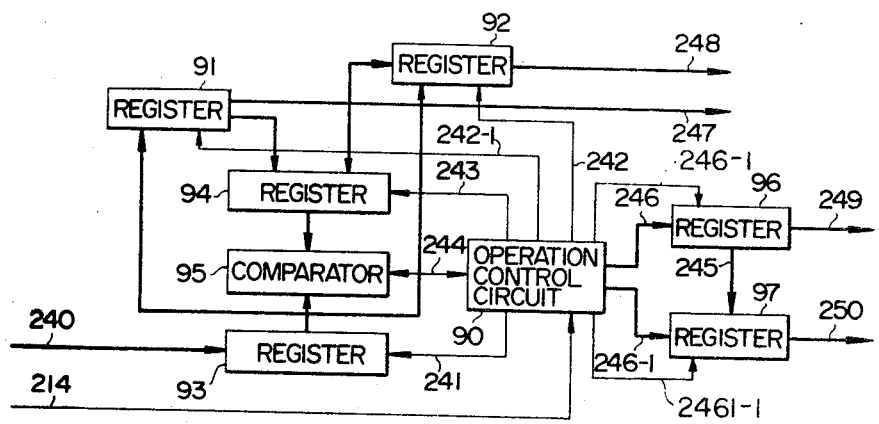
FIG. 10 is a block circuit diagram showing one example of the maximum value detector shown in FIG. 1.

With reference now to FIG. 10, when the similarity calculations at respective sampling points are commenced, the operation control circuit 90 clears the contents of a maximum value register 91 and a next to the maximum value register 92. Then the output from the similarity calculating circuit 14 is applied to a register 93 through a conductor 240. The timing of this operation is controlled by the operation control circuit 90 through a conductor 241. At the same time, an information showing that the similarity now being calculated corresponds to the sample spectrum of the white blood corpuscles of which one of the types is applied to the operation control circuit 90 through the output conductors 214. The output from the register 93 is coupled to both registers 91 and 92. The register 91 is used to store the maximum value of the similarity sent to the register 93 whereas the register 92 is used to store the value next to the maximum. When supplied with one value of the similarity the operation control circuit 90 firstly sends out a signal to the register 92, thus commanding the register 94 to transfer its content. The timings of the operations of these registers are controlled by the signals sent over conductors 242 and 243. Then the content of the register 94 is sent to a comparator 95 to be compared with the content of the register 93. The result of comparison is applied to the operation control circuit 90 through a conductor 244. Where the value next to the maximum is smaller, the operation control circuit 90 sends a signal to the register 91 now storing the maximum value. In response to this signal, the register 91 sends out its content to the register 94, and the output of the register 94 is sent to the comparator 95. If the maximum value is larger, the operation control circuit 90 produces a command signal to exchange the contents of registers 92 and 93. On the contrary, where the value of the newly received similarity is larger, the operation control circuit 90 produces a command signal requesting exchange of the contents of the registers 93 and 91 and then substituting the content of the register 94 for the content of the register 92. There are also provided a register 96 for storing the class of the white blood corpuscles corresponding to the maximum value and a register 97 for storing the type of the white blood corpuscles corresponding to the value next to the maximum. These registers 96 and 97 are controlled by the operation control circuit 90 for storing the types of the sample spectrum which varies in accordance with the result of comparison performed by the comparator 95. Where the new similarity is larger than the value of the maximum value register 91 as mentioned above, the content of the register 96 that stores the type corresponding to the maximum value is transferred to the register 97 that stores the type corresponding to the value next to the maximum through a conductor 245 and then the data of the new type are written in the register 96 through a conductor 246.

The maximum value detector 16 repeats the operation described above for a number of times equal to the number of stored sample spectra and when a termination signal is applied to the operation control circuit 90 through conductor 214, it sends out a signal to registers 91, 92, 96 and 97 thereby causing them to provide their contents on conductors 247, 248, 249 and 250, respectively.

Figure 11:
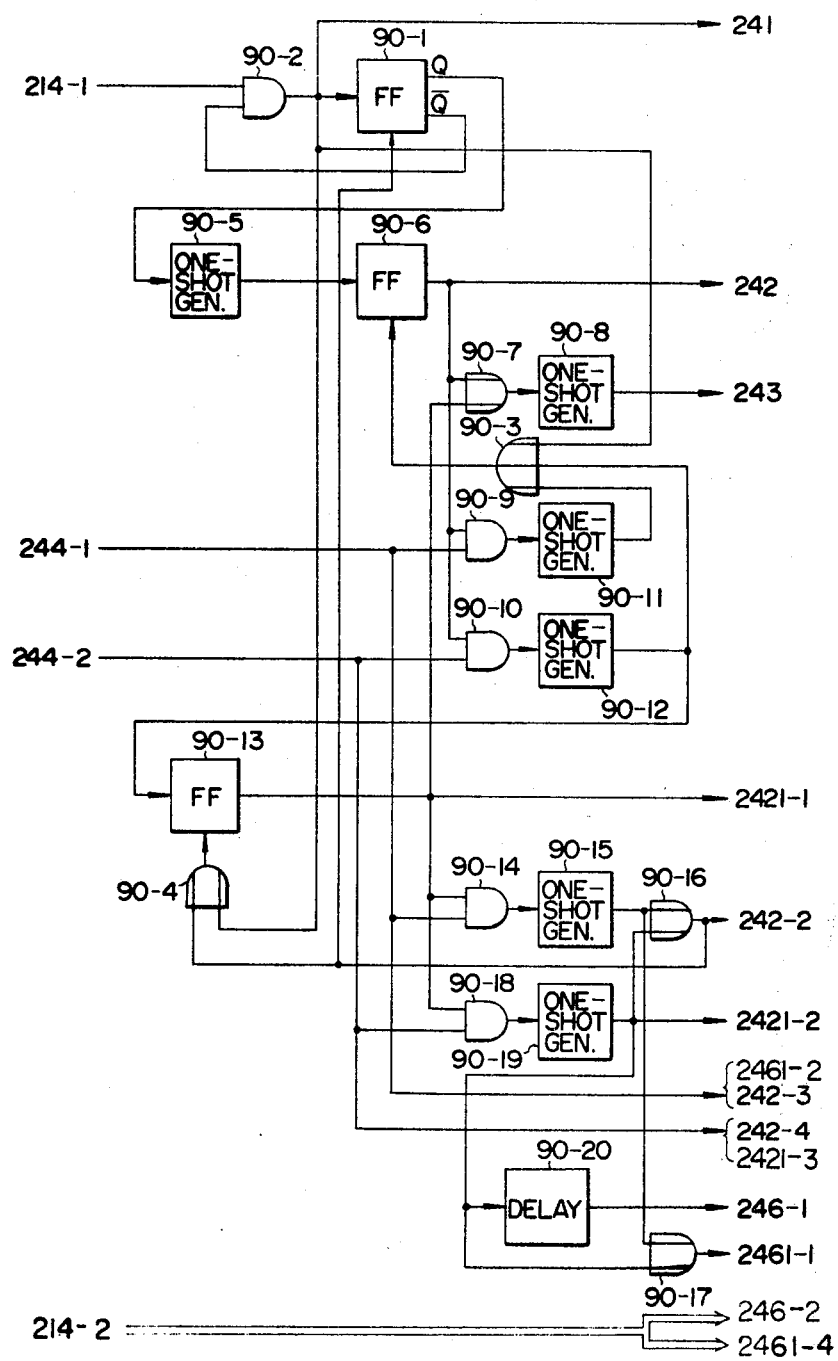
FIG. 11 is a block circuit showing one example of the operation control circuit shown in FIG. 10.

The detail of the construction of the operation control circuit 90 shown in FIG. 10 will now be described with reference to FIG. 11. When an input is applied to one input of an AND gate circuit 90-2 through a conductor 214-1 while a flip-flop circuit 90-1 is in its reset state, the AND gate circuit 90-2 is enabled by this input and the $\bar{Q}$ output of the flip-flop circuit 90-1 which is applied to the outer input of the AND gate circuit 90-2 whereby the output thereof is sent to a conductor 241 and OR gate circuits 90-3 and 90-4. This output is also sent to the flip-flop circuit 90-1 thus setting the same. The output applied to the conductor 241 is sent to the register 93 thereby storing the data from the conductor 240 in the register 93. A conductor 214-1 is used to apply the output from the AND gate circuit 12-22 in the memory control circuit 12 shown in FIG. 5 to one input of the AND gate circuit 90-2. More particularly, in the circuit shown in FIG. 5, when the one-shot generator 12-13 produces an output while the flip-flop circuit 12-7 is maintained in its set condition, the AND gate circuit 12-22 is enabled to provide an output on the conductor 214. When the flip-flop circuit 90-1 is set, the one-shot generator 90-5 will be driven at the build-up portion of its Q output thereby setting the flip-flop circuit 90-6. When one value of similarity is received the content of register 92 is transferred into the register 94 by a signal sent to the register 92 from the flip-flop circuit 90-6 through a conductor 242-1. The output from the flip-flop circuit 90-6 is sent to one-shot generator 90-8 through an OR gate circuit 90-7 and the output from the one-shot generator 90-8 is sent to the register 94 over the conductor 243, whereby the data from the register 92 are stored in the register 94. The result of comparison of the data from registers 93 and 94 performed by a comparator 95 is sent to AND gate circuits 90-9 and 90-10 through conductors 244-1 and 244-2, respectively. Since the flip-flop circuit 90-6 has been set the outputs from the AND gate circuits 90-9, 90-10 are applied to a one-shot generators 90-11 and 90-12 respectively thereby driving these generators. The flip-flop circuit 90-6 is reset by the output from the one-shot generator 90-11, whereas the flip-flop circuit 90-13 is set by the output from the one-shot generator 90-12. Where the content of register 94 is larger than that of the register 93, an output is produced on conductors 244-1 thus resetting the flip-flop circuit 90-6. On the contrary, when the content of the register 94 is smaller than that of the register 93, flip-flop circuit 90-13 is set to provide a signal to the register 91 through a conductor 2421-1.

As a result, in the register 94 is stored a maximum value which is then compared with the content of the register 93. When the content of the register 93 is smaller than that of the register 94 a conductor 244-1 is logically selected to enable the AND gate 90-14. Pulse signals are delivered from the one-shot generators 90-15 and are applied to the register 92 to set the content of the register 93 to the register 92 as a new content thereof. At the same time, said pulse signals from the one-shot generator 90-15 are also sent to a conductor 2461-1 to store into the register 97 data representing the class of the white blood corpuscles corresponding to the value next to the maximum. On the contrary, when the content of the register 94 is smaller than that of the register 93 a conductor 244-2 is logically selected to enable the AND gate 90-18. Pulse signals are delivered from the one-shot generator 90-19 and are applied to conductors 2421-2, 242-2 to send the contents of the registers 93, 94 to the registers 91, 92. At the same time, said pulse signals are sent to the conductor 2461-1 to transfer the content of the register 96 to the register 97 and are applied to a delay circuit 90-20. The delayed pulse signals from the delay circuit 90-20 are sent to the conductor 246-1 and a new content is sent to the register 96.

Figure 12:
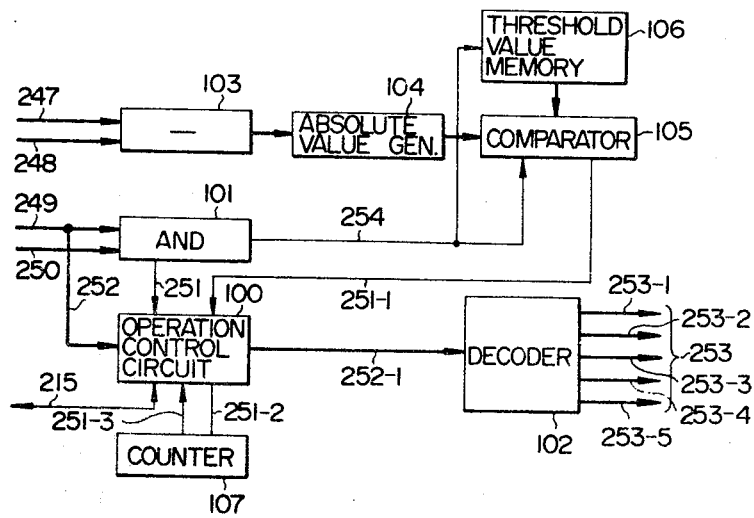
FIG. 12 is a block circuit diagram showing one example of the judgment circuit shown in FIG. 1.

The maximum value and the value next to the maximum which are detected by the maximum value detector 16 are sent to the subtractor 103 in a judgment circuit 17 shown in FIG. 12 from registers 91 and 92 through conductors 247 and 248. The judgment circuit 17 is constructed such that a signal informing that the calculation of the similarity between all sample data and input data has been terminated is applied to the operation control circuit 100 from the memory control circuit 12 through the conductor 215. The judgment circuit 17 firstly determines that whether the type of the sample corresponding to the maximum value is the same as the type of the sample corresponding to the value next to the maximum or not in accordance with the maximum value and the value next to the maximum of the similarity S which is an information applied by the maximum value detector 16, the type of the sample corresponding to the maximum value, and the type of the sample corresponding to the value next to the maximum. Upon coincidence, the judgment circuit 17 judges that the class of the point now being processed corresponds to the maximum value and sends a signal to a counting circuit 18. On the contrary, if the type of the sample corresponding to the maximum value and the type of the sample corresponding to the value next to the maximum are not the same, the judgment circuit 17 functions to calculate the difference between the maximum value and the value next to the maximum of the similarity S and then compares this difference with a predetermined threshold value $\theta$. Where the difference is larger than the threshold value $\theta$ the judgment circuit 17 sends a signal corresponding to the class obtained by the maximum value detector 16 to the counting circuit 18. On the other hand, if this difference is smaller than the threshold value $\theta$ and when this point is a point at an intermediate point of one scanning line the judgment circuit 17 determines that it is impossible to judge this point and that the judgment of the next point should be followed and transmits a judgment termination signal to the memory control circuit 12 through a conductor 215. Generally, the value of the threshold value $\theta$ is set to be less than 0.1. When the point is on an edge of the picture, the judgment circuit 17 determines that it is the background and sends a signal to the counting circuit 18. This operation is repeated until the memory control circuit 12 completes the calculation of the similarity regarding the similarity of all of 10 × 150 sampling points. When the calculation for 10 × 150 sampling points is completed, the judgment of the subarea containing next 10 × 150 points is commenced. The counting circuit 18 is provided with a plurality of counters for respective classes of the white blood corpuscles so that whenever a judgment information is supplied by the judgment circuit 17 the count of the counter of the class corresponding to the judgment is advanced one step.

There will now be described in detail the operation of the operation control circuit of FIG. 12 by referring to the circuit of FIG. 13. When a pulse signal representing that similarity calculations with respect to all the reference spectral data have been completed is sent to the conductor 215-1, a flip-flop circuit 100-4 is set and a flip-flop circuit 100-6 is reset by said pulse signal. When the judgment circuit is set to an operation state with the set of the flip-flop 100-4, a resultant of the comparison between the classes corresponding to the maximum value and the value next to the maximum performed at the AND gate 101 shown in FIG. 12 is conducted to the judgment circuit through a conductor 251. If the coincidence therebetween is obtained an AND gate 100-8 is enabled to generate a signal for driving a one-shot circuit 100-10 to deliver a pulse signal. Where the content of the counter 107 of FIG. 12 counting the number of the rejected cells is 0 the output of the comparator 100-22 becomes 1 to enable an AND gate 100-24. The output of the AND gate 100-24 opens the gate of the gate circuit 100-16 to send an output to a conductor 2521 therefrom. On the contrary, if the content of the counter 107 is not 0 the flip-flop 100-6 is set and clock pulses are applied through an AND gate 100-14 to the gate circuit 100-16 till the content of the counter 107 of FIG. 12 becomes 0. When the content of the counter 107 is set at 0 the comparator 100-22 generates an output signal. The one-shot circuit 100-25 generates an output in response to the build-up portion of the output signal of the comparator 100-22. As the result, pulse signals having the number larger by 1 than the content of the counter 107 of FIG. 12 are sent to the gate 100-16 via an OR gate 100-15.

Whereby the data sent from the conductor 252 and representing the class of the sample corresponding to the maximum value are applied to the decoder 102 through a conductor 2521. The decoder 102 produces a pulse on a corresponding output conductor, for example a conductor 253-1 among a group of signal conductors 253 representing the types of the white blood corpuscles. At this time, if the contents of the data on the conductors 249 and 250 were not the same the AND gate circuit 101 will produce an output on the conductor 254.

The output conductor 247 of the register 91 adapted to store the maximum value and the output conductor 248 of the register 92 adapted to store the value next to the maximum are connected to subtraction circuit 103 so as to obtain the difference therebetween, which is applied to an absolute value calculating circuit 104 to determine the absolute value of the difference. The absolute value thus determined is sent to a comparator 105. When a signal indicating that the classes of the white blood corpuscles corresponding to the maximum value and the value next to the maximum respectively are not the same is applied to the comparator 105 from the AND gate circuit 101 through the conductor 254, the comparator 105 compares the maximum value sent from the absolute value calculating circuit 104 with the threshold value $\theta$ stored in the threshold value memory device 106 and the result of the comparison is sent to the operation control circuit 100 over a conductor 2511. When the absolute value or the difference between the maximum value and the value next to the maximum is larger than the threshold value, the signal on the conductor 2511 becomes to 0 so that the 1 signal from the inverter 100-17 is applied to one input of the AND gate circuit 100-7. Accordingly, as described hereinabove, the gate circuit 100-16 is enabled or opened by the signal from the OR gate circuit 100-15 for sending the data regarding the classes of the white blood corpuscles to the decoder 102 which acts to produce pulses on the corresponding conductors in group 253.

On the contrary, where the difference is less than the threshold value an AND gate circuit 100-18 is enabled to produce a command signal on a conductor 2512-1 which advances one count the content of an up-down counter 107 that is used for the purpose of counting the number of sampling points of the image which are difficult to judge. The signal on the conductor 2511 is also applied to the other input of the AND gate circuit 100-2 for driving the one-shot generator 100-19 by the output from the AND gate circuit 100-2. The output from the one-shot generator 100-19 is applied to the flip-flop circuit 100-4 through an OR gate circuit 100-20 for resetting the flip-flop circuit 100-4. The output from the one-shot generator 100-19 is also applied to a conductor 2512-2 through OR gate circuit 100-21 and directly to conductor 215-2. The signal applied to the conductor 215-2 is impressed upon one input of an AND gate circuit 12-23 of the memory control circuit 12 shown in FIG. 5, the other input of the AND gate circuit 12-23 being connected to receive the output of the comparator 12-25 which compares the output of a 150-step counter 12-9 with the content of a register 12-24.

Thereafter the continuous points of the image which were difficult to be judged and counted by the counter 107 are judged that they belong to the same class as the firstly judged point. Accordingly, at a time when the firstly judged point is reached the content of the counter 107 is counted down to zero, and the number of the points which could not be judged is sent to comparator 100-22 in the operation control circuit 100 over a conductor 2513. When the input to the comparator 100-22 coincides with the content of the register 100-23, the comparator 100-22 produces an output for driving a one-shot generator 100-25. This output is also applied to one input of an AND gate circuit 100-24 and an inverter 100-12. The operation control circuit 100 sends to decoder 102 signals corresponding to the classes and having the same number as the count of the counter 107 thus causing the decoder 102 to produce a pulse train on a corresponding conductor of the conductor group 253. When the content of the counter 107 is reduced to zero the operation control circuit 100 sends a command signal to decoder 102 thus causing it to produce one pulse corresponding to the present point.

As the number of processes of a picture having 150 × 150 sampling points reaches a predetermined number, an estimation circuit 19 is driven which calculates the percentages of the white blood corpuscles of respective classes with respect to the total number of the white blood corpuscles in the entire area of the picture and sends the result of calculation to a display device 20. When the result is displayed, the transfer mechanism 3 is operated to house the examined slide in the cassette 1 and to set a new slide on the stage of the microscope. Similar operation is repeated for all slides of the number of 50, for example.

FIG. 14 shows one example of the estimation circuit 19 which is constructed to estimate the numbers of the white blood corpuscles of respective classes on the theory of statistics. The theory will be discussed firstly. Suppose now that there are N things A whose distribution of area S can be defined by a density function P(S). If N is sufficiently large, the mean value $Sm$ of S could be expressed by an equation $$Sm = \int_0^\infty S \cdot P(S) ds \quad (4)$$

Let us assume that the spacing of most of the areas $S$ of the thing $A$ ranges between 0 and $S_M$. By dividing this spacing by $n$ and by putting $\Delta S = S_M/n$ and $Si = i\Delta S$, $i = 0, 1, 2 \ldots n$, then equation (4) can be expressed approximately by $$Sm \approx \sum_{i=0}^{n-1} Si \cdot P(Si) \Delta S \quad (5)$$

By denoting the number of things $A$ having their areas between $Si$ and $Si+1$ as $Ni$, and by assuming that $N$ is sufficiently large, we obtain $$P(Si) \Delta S = Ni/N \ldots (6)$$

Accordingly the equation (5) can be modified as $$Sm \approx \sum_{i=0}^{n-1} Si \frac{Ni}{N} \quad (7)$$

A term $$\sum_{i=0}^{n-1} SiNi$$

represents the total area of $A$ when the number of $A$ counted is equal to $N$. In other words, equation (7) is the equation that can be used to estimate the mean area of $A$ of the number equal to $N$. Conversely, if $Sm$ were known the estimated value $\hat{N}$ of the number $N$ of $A$ can be estimated according to the following equation where the total area of A is equal to $S_T$ $$\hat{N} = S_T/Sm \ldots (8)$$

Where the distribution of P(S) is normal it is also possible to detect the error, and the square means relative error $V(\hat{N}, N)$ can be given by an equation, $$V(\hat{N}, N) = \frac{1}{N} \frac{\delta^2 S}{S^2 m} \quad (9)$$

where $\delta S$ represents a standard deviation of the normal distribution P(S). Equation (9) shows that where $N$ is large or $\delta S/Sm$ is small it is possible to estimate the number of $A$ at a considerably high accuracy. By simulation, a value of $N$ of about 250 was obtained when $\delta S/Sm = 0.4$ at an error of about 2%.

Actually, the estimation of the area is made by spotting area $d^2$ as above described. Accordingly, in equation (8), $S_T$ can be represented by $d^2 N_T$, where $N_T$ represents the total number of spots contained in $A$. By putting $Sm/d^2 = Nm$, equation (8) becomes $$\hat{N} = N_T/Nm \ldots (10)$$

Under these conditions, the smaller is $d^2/Sm$, more excellent is the result. However, by simulation, it is found that $d^2/Sm = 0.1$ is sufficient.

FIG. 14 shows a circuit that operates equation (10), in which reference numerals 110, 112, 114, 116 and 118 represent memory devices which store the number of spots corresponding to the mean areas of respective classes of the white blood corpuscles. Actually, however, since the spectrum of the cellar substance of the white blood corpuscles is effective for classification, these areas represent the area of the cellar substance. There are also provided division circuits 111, 113, 115, 117 and 119, and a pulse generator 120 which, in response to a signal sent over a conductor 218 and commanding a calculation, sends an operation initiation pulse to respective division circuits 111, 113, 115, 117 and 119 through a conductor 256. The division circuits 111, 113, 115, 117 and 119 operate to divide by the number of spots which have been stored in respective memory devices 110, 112, 114, 116 and 118 the numbers sent from the counting circuit 18 respectively over conductors 255-1, 255-2, 255-3, 255-4 and 255-5, said numbers being specific to respective classes of the white blood corpuscles. The respective division circuits 111, 113, 115, 117 and 119 send the result of division to the display device 20 in the succeeding stage over a group of conductors 257.

FIG. 15 is a flow chart showing the operation of the novel apparatus of this invention. The focus of the microscope is adjusted by using a filter for a wavelength of 530 nm because the light transmissivity of the slide itself or the background ranges from about 65 to 80% as shown in FIG. 3F whereas the transmissivity of the white blood corpuscles of various types is a minimum at a wavelength of 530 nm so that it is advantageous to adjust the focus at a point where the contrast of the white blood corpuscles with reference to the background is the maximum. In FIG. 15, a reference character M shows the number of the subareas where a picture including 150 × 150 points is divided into 15 subareas each containing 10 × 150 points. Accordingly when the number of M is increased to 15, it is seen that the processing of one picture has been completed.

What we claim is:

1. Apparatus for discriminating the type and counting the number of white blood corpuscles comprising means for irradiating with light a predetermined area of a slide supporting stained white blood corpuscles, means for producing a microscopic image of said white blood corpuscles which is analyzed into a plurality of given wavelength components over the entire range of visible light, means for producing an electric signal corresponding to the density of light transmitted through each sampling point of the resulting microscopic image of each of said plurality of wavelength components, a memory device for storing said electric signal, means for normalizing said electric signal, means for comparing the normalized electric signal and a reference data signal established for each type of said white blood corpuscles and producing a similarity signal indicating the similarity, means for detecting and storing a first similarity signal corresponding to the maximum similarity and a second similarity signal corresponding to the next maximum similarity thus determined and for detecting and storing the type of the white blood corpuscles corresponding to said maximum value and the type of the white blood corpuscles corresponding to said value next to the maximum, means responsive to the result of said detections for counting the number of the white blood corpuscles at respective sampling points, and means for estimating the number of the white blood corpuscles of respective types in a predetermined area of said slide.

2. The apparatus as claimed in claim 1 wherein said means for producing said microscopic image comprises a microscope, an optical system for said microscope, and a rotary type interference filter included in said optical system for an analyzing visible light having a wavelength of from 400 nm to 700 nm into wavelength components at a spacing of predetermined wavelength.

3. The apparatus as claimed in claim 1 wherein said means for producing said electric signal comprises a photoelectric transducer for producing a video signal having a level corresponding to the tone of a microscopic image of each wavelength, and an analogue-digital converter for converting said video signal into a digital signal corresponding to the tone at a predetermined sampling point in said microscopic image.

4. The apparatus as claimed in claim 1 wherein said memory device comprises means for dividing said picture image into a plurality of subareas each containing sampling points of the number equal to the number obtained by dividing the total number of sampling points in said microscopic image by an integer, and a memory circuit for accumulating and storing a plurality of the data in each subarea.

5. The apparatus as claimed in claim 1 wherein said normalizing means comprises a first gate circuit connected to receive the data stored in said memory device, an operation control circuit for controlling the operation of said first gate circuit, a first memory device for storing one set of data provided by said first gate circuit, a second gate circuit connected to receive the data stored in said first memory device, a third gate connected to receive a data succeeding the data stored in said first memory device, first and second squaring circuits for producing squares of the output data from said second and third gate circuits, a first multiplying circuit and a first addition circuit respectively impressed with the output data from said second and third gate circuits, first, second, third and fourth accumulator-adders respectively accumulate and add the outputs from said first and second squaring circuits, said first multiplying circuit and said first addition circuit, circuit means for detecting the minimum value of the data passed through said first gate circuit, a first subtraction circuit for obtaining the difference between the detected minimum value and the output from said fourth accumulator-adder, a first coefficient memory device storing a predetermined constant, a second multiplying circuit for obtaining the product of the content of said first coefficient memory device and said minimum value, a third multiplying circuit for obtaining the product of the output from said second multiplying circuit and the output of said second subtraction circuit, a second addition circuit for adding the output from said third multiplying circuit and the outputs from said first, second and third accumulator-adders, a second coefficient memory device for storing a predetermined constant, a fourth multiplying circuit for obtaining the product of the content of said second coefficient memory device and the output of said second addition circuit, circuit means for obtaining the square root of the output of said fourth multiplying circuit, a second subtraction circuit for obtaining the difference between the input data applied to said first gate circuit and said minimum value detected, and a division circuit for dividing the output from said second subtraction circuit by the output from said circuit means for obtaining the square root.

6. The apparatus as claimed in claim 5 wherein said operation control circuit comprises first, second, third and fourth signal input conductors, a one-shot generator connected to said first signal input conductor for applying a driving signal to said second addition circuit, said second coefficient memory circuit, said fourth multiplying circuit, said first coefficient memory circuit and said second multiplying circuit, a first AND gate circuit connected to said first and third input conductors, a second AND gate circuit connected to said second and third conductors and an inverter connected to said fourth input conductor.

7. The apparatus as claimed in claim 5 wherein said minimum value detecting circuit means comprises a register for storing input data, a comparator for comparing the content of said register and new input data, and control means including an AND gate circuit which, when the newly applied data are smaller than the content of said register, applies a load signal to said register for substituting said smaller data for the content of said register.

8. The apparatus according to claim 1 wherein said means for determining similarity comprises a reference data memory device in which reference data have been stored and a circuit for calculating the similarity between the reference data stored in said reference memory and said normalized input data.

9. The apparatus as claimed in claim 8 wherein said similarity calculating circuit comprises a first memory device for storing one set of data from said normalizing circuit, a second memory circuit for storing one set of said reference data, a first addition circuit for adding the content of said first memory device to succeeding data, a second addition circuit for adding the content of said second memory device to succeeding data, a first multiplier for multiplying the outputs from said first and second addition circuits, a second multiplier for multiplying the contents of said first and second memory devices, a third multiplier for multiplying two data succeeding the data stored in said first and second memory devices, first, second and third accumulator-adders for accumulating and adding the respective outputs of said first, second and third multipliers, a third addition circuit for adding together the outputs of said first, second and third accumulator-adders, a coefficient memory device for storing a predetermined constant, and a fourth multiplier for obtaining the product of the output of said coefficient memory device and the output of said third addition circuit.

10. The apparatus as claimed in claim 1 wherein said maximum value detecting circuit comprises a first register for storing the output data from said similarity calculating circuit, a maximum value register and a next to the maximum value register respectively storing the content of said first register, a second register to which the contents of said maximum value register and said next to the maximum value register are to be transferred, a comparator for comparing the contents of said first and second registers, a third register for storing the data representing the types of the white blood corpuscles regarding the data stored in said maximum value register, and a fourth register for storing the data representing the types of the white blood corpuscles regarding the data stored in said next to the maximum value register.

11. The apparatus as claimed in claim 1 wherein said detecting and memory means includes a judgment circuit for judging the identity between the type of said maximum value and the type of said value next to the maximum.

12. The apparatus as claimed in claim 1 wherein said judgment circuit comprises a subtraction circuit for obtaining the difference between said maximum value and said value next to the maximum, a circuit for determining the absolute value of the output of said subtraction circuit, a threshold value setting circuit, a comparator for comparing the threshold value set thereby and said absolute value, an AND gate circuit for determining the logical product of the data representing said maximum value and said value next to the maximum, and a decoder for producing a signal which represents the type of the white blood corpuscles when said AND gate circuit produces an output.

13. The apparatus as claimed in claim 1 wherein said means for estimating the number of the white blood corpuscles comprise a plurality of memory devices for storing the number of spots corresponding to the area of the cellar substance of respective types of the white blood corpuscles and a corresponding number of division circuits for dividing the contents of said plurality of memory devices by the output from said means for counting the number.

* * * * *